United States Patent [19]

Smith

[11] 4,252,678

[45] Feb. 24, 1981

[54] PREPARATION OF COLLOIDAL DISPERSIONS OF RUTHENIUM, RHODIUM, OSMIUM AND IRIDIUM BY THE POLYMER-CATALYZED DECOMPOSITION OF CARBONYL CLUSTER COMPOUNDS THEREOF

[75] Inventor: Thomas W. Smith, Penfield, N.Y.

[73] Assignee: Xerox Corporation, Stamford, Conn.

[21] Appl. No.: 100,311

[22] Filed: Dec. 4, 1979

[51] Int. Cl.$^3$ .................. B01J 31/02; C08K 3/08
[52] U.S. Cl. .................. 252/430; 260/42.22; 430/286; 430/945; 568/451; 568/454; 568/455
[58] Field of Search .............. 260/604 HF, 42.22; 252/430; 430/945, 286

[56] References Cited

U.S. PATENT DOCUMENTS

| | | | |
|---|---|---|---|
| 3,228,881 | 1/1966 | Thomas | 260/39 M |
| 3,281,344 | 10/1966 | Thomas | 260/42.22 |
| 3,998,864 | 12/1976 | Trevillyan | 260/604 HF |
| 3,998,887 | 12/1976 | Allen | 260/604 HF |

*Primary Examiner*—John F. Niebling
*Attorney, Agent, or Firm*—H. M. Brownrout; E. O. Palazzo; P. P. Eichler

[57] ABSTRACT

There is disclosed a method for the preparation of a homogeneous, physically stable dispersion of colloidal metal particles of a transition metal selected from the group consisting of ruthenium, rhodium, osmium and iridium, having a size in the range of from about 10 Angstrom units to about 200 Angstrom units. The method comprises preparing a solution of a functional polymer in an inert solvent, and incrementally adding thereto a transition metal cluster compound at a temperature at which the transition metal cluster compound will become bound to the polymer and thermally decompose to produce elemental transition metal particles, the process being carried out in an inert atmosphere. Such dispersions may be used per se as catalysts, or may be used for the preparation of supported colloidal transition metal catalysts. The dispersions may also be used for the preparation of ablative optical recording media.

47 Claims, No Drawings

PREPARATION OF COLLOIDAL DISPERSIONS OF RUTHENIUM, RHODIUM, OSMIUM AND IRIDIUM BY THE POLYMER-CATALYZED DECOMPOSITION OF CARBONYL CLUSTER COMPOUNDS THEREOF

The present invention relates to a novel method for the preparation of homogeneous colloidal elemental dispersions of a transition metal selected from the group consisting of ruthenium (Ru), rhodium (Rh), osmium (Os) and iridium (Ir), with the use of a functional polymer in dilute solution in any of a large variety of suitable inert solvents, and with the use of any suitable large molecule transition metal cluster compounds. The invention also relates to the homogeneous colloidal elemental transition metal dispersions, to their use as catalysts and for the preparation of supported transition metal catalysts, and to their use as materials for the preparation of ablative optical recording media. The term "transition metal" as used herein refers to a transition metal selected from the group consisting of ruthenium, rhodium, osmium and iridium unless otherwise stated.

In general, the preparation of the homogeneous colloidal elemental transition metal dispersions of the invention involves the thermal decomposition of a suitable large transition metal cluster compound in a relatively dilute solution of a functional polymer in an inert solvent for the transition metal cluster compound and the polymer, the reaction being carried out in an inert atmosphere, with the thermal decomposition of the transition metal cluster compound occurring primarily with the cluster bound to the functional polymer. The functional polymer can react with the transition metal cluster in either an "active" or "passive" fashion; i.e., it may react directly and spontaneously with the large transition metal cluster compound without the prior loss of any ligand (active); it may react with the transition metal cluster compound only after it has lost at least one ligand (passive); or both processes may occur simultaneously. The term "functional polymer" includes both "active" and "passive" polymers. Whether the reaction proceeds actively or passively or both simultaneously depends upon the particular transition metal cluster compound and polymer employed. The term "passive polymer" refers generally to polymer molecules substantially each of which contains at least one reactive binding site for the transition metal cluster compound at which sites the transition metal cluster compound reacts to produce polymer-bound transition metal clusters. Such passive polymers are to be distinguished from "active polymers" in that systems for the preparation of colloidal transition metal dispersions employing a passive polymer in solution require sufficient heat or other stimulus to remove at least one ligand from the transition metal cluster compound before the cluster can become bound to the polymer; that is, the transition metal cluster compound cannot react directly and spontaneously with the binding sites of the passive polymer, but only after loss of one or more ligands. Active polymers do not require such a prior loss of ligands, and the transition metal cluster compound reacts directly and spontaneously with their reactive binding sites. Preferably, the appropriate amount of the desired functional polymer is dissolved in the appropriate amount of the desired inert solvent, and the solution is heated to the appropriate reaction temperature at which thermal decomposition of the polymer-bound transition metal cluster compound will occur, whereupon the appropriate amount of the desired transition metal cluster compound is added in appropriate increments and binds to the polymer. This incremental addition is continued until the appropriate total amount of transition metal cluster compound has been added and permitted to thermally decompose.

Depending upon the choice of inert solvent, polymer, transition metal cluster compound, and the preparative conditions, homogeneous colloidal transition metal dispersions of the invention may contain colloidal metal particles having an overall size range of from about 10 Angstrom units to about 200 Angstrom units. Usually, however, the materials and conditions are selected such that any given dispersion produced will inherently have a relatively narrow particle size range within the overall range of from about 10 Angstrom units to about 200 Angstrom units, the materials and conditions being selected to produce a particle size range suitable for the intended end use of the dispersion. As a practical upper limit, the particle size is typically about 200 Angstrom units, since colloidal transition metal dispersions according to the invention having such a maximum particle size are typically very physically stable; that is, they do not settle in periods of years. If the particle size substantially exceeds about 200 Angstrom units, the dispersions tend to lack physical stability and may flocculate. Dispersions having a maximum particle size of about 150 Angstrom units have the best physical stability. The colloidal transition metal dispersions according to the invention are also very chemically stable if kept in an inert environment such as argon. Extensive oxidation of the transition metal particles may occur readily in the presence of oxygen.

Considering the possible catalytic utilities of the colloidal transition metal dispersions of the instant invention, it is known that the catalytic activity of colloidal transition metal particles is usually inversely proportional to the size of the particles. Accordingly, the most efficient particle size for catalytic use may be in the minimum size range. There are, however, two features of the use of dispersions of this invention as catalysts which outweigh simple considerations of particle size in the efficiency of the catalyst. This invention provides a method for the preparation of discrete colloidal particles of controlled narrow particle size distribution. These dispersions can subsequently be immobilized in an appropriate solid phase to yield a solid catalyst which contains a high loading of colloidal catalytic particles. In processes where the colloidal particles are generated in situ, i.e., on the support, by reduction of adsorbed ions, high percentages of catalyst loading cannot be achieved while maintaining a small particle size and a narrow particle size distribution. The most important feature of the catalytic activity of the dispersions of this invention is the role of the polymer bound to the particles' surfaces. In the presence of reducing gases, the functional sites on the polymer can react with the transition metal atoms to generate the active catalytic species in a liquidous layer surrounding the particle. The colloidal transition metal dispersions may not only be used as catalysts per se; they may also be supported in a suitable solid support. Various reactions which may be catalyzed by the colloidal transition metal of the invention include hydroformylation reactions, oxidative coupling and hydrogenation of alkenes.

For the preparation of ablative optical recording media, it is preferred generally to maximize the particle size up to about 200 Angstrom units; it is also desirable to maximize the ratio of colloidal transition metal to the polymer, which may be accomplished by minimizing the amount of polymer and maximizing the amount of transition metal cluster compound during the incremental addition of the transition metal cluster compound. The basic reason for this is to maximize the light absorptivity of the films cast from the dispersions. Ablative optical recording media which may be prepared from colloidal transition metal dispersions according to the instant invention are described in copending U.S. patent application Ser. No. 054,204, filed July 2, 1979, entitled "Optical Disk", which application is assigned to the assignee of the instant application.

Considering the method of producing homogeneous colloidal transition metal dispersions according to the invention in greater detail, a suitable solvent is required which will dissolve the functional polymer and the transition metal cluster compound and the transition metal cluster compound becomes bound to the reactive sites of the polymer. The bound transition metal cluster tends to decompose to the metal at a rate which is greatly in excess of the rate of any decomposition of unbound transition metal cluster compound.

Considering suitable functional polymers in greater detail, it has already been indicated that a suitable polymer is any polymer which contains one or more reactive binding sites which will react with the transition metal cluster compound to yield polymer-bound transition metal clusters. It is highly preferred that this binding occur much more rapidly than any substantial decomposition to metallic transition metal of unbound cluster compound remaining dissolved in the solvent. It is also highly preferred that the polymer-bound transition metal cluster decomposes at a much more rapid rate than the unbound cluster compound. This insures that the transition metal particles will be generated primarily in the domain of the polymer molecules.

The ratio of polymer to solvent employed is important. The concentration of the polymer must be below the critical entanglement concentration for the polymer molecules in solution, that is, each polymer molecule constitutes a discrete entity. Each such discrete polymer molecule may be referred to as an isolated domain. The lower the molecular weight of the polymer, the higher the critical entanglement concentration for the polymer, thus the greater the amount of polymer which can be used for a given volume of solvent.

As will be seen from the examples which follow, the transition metal cluster compound is preferably added in increments, so that a predetermined amount of transition metal cluster compound is present in solution. The mechanism and general sequence of events in the reaction mixture is somewhat as follows. When a relatively small increment of transition metal cluster compound is added to a solution of the polymer at an appropriate temperature, the polymer first serves as a reactant, and the transition metal cluster compound becomes bound to the binding sites of the polymer. This reaction preceeds nucleation, wherein a particle nucleus is formed which may either be a transition metal or some more complex transition metal-containing species. Thus, at the outset of the entire sequence of events, the functional polymer is a catalyst for the generation of transition metal particle nuclei or transition metal-containing particle nuclei, which are bound to the reactive sites of the polymer. At this point, the polymer has served its catalytic role for the nucleation of particles, and the reaction vessel contains randomly dispersed colloidal nuclei of a transition metal or transition metal-containing particles bound to the reactive sites of the polymer. At nucleation, the decomposition becomes dominated by a new process, viz., disproportionation of transition metal cluster compound at the surfaces of the nuclei. The polymer stabilizes the nascent (growing) particles in the same domains in which the particles were nucleated, that is, collisional growth of the nascent particles is minimized. The principal role of the polymer now becomes stabilization of the newly formed colloidal transition metal dispersion. Now the reaction merely enlarges the particles as more transition metal cluster compound is added incrementally and reacts at the surface of the polymer-bound particles. There is a distinct transformation from the particle nucleation stage to the particle growth stage, evidenced by a dramatic change in the rate of evolution of carbon monoxide.

The number of polymer molecules, i.e., discrete polymer molecule domains, is directly proportional to the number of transition metal particles and inversely proportional to the particle size at any given volume of metal.

Suitable functional polymers must, of course, be soluble in the solvent selected, preferably at about ambient temperature or slightly above for convenience, but in any event, necessarily at the temperature at which the transition metal cluster compound binding and decomposition occur to produce colloidal transition metal particles. There are a number of polymers which may be used in the method of the instant invention. Such would include polymers bearing groups which non-oxidatively substitute transition metal carbonyls. Typical polymers of this type are vinyl type polymers containing alkenyl, phosphine, phosphine oxide, arsine, isonitrile and isocyanate groups. Typical examples of such polymers are copolymers of (1) styrene, ethylene, or derivatives thereof, with (2) butadiene, isoprene, cyclopentadiene, parastyryldiphenylphosphine and para-styryldiphenylphosphine oxide.

Turning now to a consideration of suitable transition metal cluster compounds, such are labile transition metal carbonyl clusters. In referring to such compounds, the term "labile" as used herein is intended to signify that the carbonyl ligands in the compound readily become dissociated from the molecule to leave the elemental transition metal. These large transition metal carbonyl cluster compounds are characterized by containing already-formed metal-to-metal bonds. The specific class of suitable labile large transition metal carbonyl cluster compounds includes, for example, hexarhodiumhexadecacarbonyl, tetrarhodiumdodecacarbonyl, tetrairidiumdodecacarbonyl, triosmiumdodecacarbonyl, and trirutheniumdodecacarbonyl. The suitable transition metal carbonyl cluster compounds are either commercially available or may be prepared by methods disclosed in the literature.

If the selected transition metal cluster compound is a liquid, it can be added directly to the reaction mixture in the appropriate increments. On the other hand, if the transition metal cluster compound is a solid, as is typically the case with these large molecules, it may first be dissolved in a small amount of a suitable solvent for incremental addition, or it may be added as a powder with, for example, a powder dosing funnel.

As has been mentioned, and as will be seen from the examples, the transition metal cluster compound should be added incrementally at suitable time intervals. As already indicated, the reason for this incremental addition is that two separate reactions can occur simultaneously. First, if too much cluster compound is added, some of it remains in solution, where it can decompose slowly to metal. Decomposition of the unbound transition metal cluster compound is undesirable and should be minimized. Second, the preferred reaction is the decomposition of the polymer-bound transition metal species, and the incremental addition and the rate thereof should be adapted to favor this reaction.

As a minimum first increment of transition metal cluster compound, an amount may initially be added which is just enough to saturate all of the reactive binding sites on the polymer. With these large cluster compounds, the increments are, indeed, nearly stoichiometric, this preference existing because any decomposition of unbound metal cluster molecules will rapidly lead to the formation of free particles.

The increments are added based upon monitoring the evolution of carbon monoxide which occurs as a result of the decomposition of the transition metal cluster compound. When little carbon monoxide is being generated from the reaction mixture, it is apparent that the cluster compound present in the reaction mixture has substantially decomposed. Thus, it is desirable to wait until only a little or no carbon monoxide is being generated, then add another increment of up to about 5 to about 10 moles excess, and so on, until the addition of the final increment. Typically, it has been found that it is desirable to wait for a period of about 2 to about 4 hours between increments, depending upon the reaction rate, which is a function of the reagents, solvent, temperature and other conditions.

After the last increment has been added, it is generally convenient to continue heating, for example, for about 24 hours to evolve the last traces of carbon monoxide, indicating substantially total completion of the desired reaction. Of course, it is possible to add increments less frequently than indicated above. On a production basis, it would be preferred to add the transition metal cluster compound continuously at a rate determined to be sufficient to compensate for the consumption of the cluster compound in the reaction vessel; this would be the equivalent of a continuous incremental addition.

The maximum amount of transition metal cluster compound which can effectively be added to the dispersion is determined experimentally by the point at which the total transition metal concentration in the dispersion can no longer be increased significantly. Immediately following particle nucleation, the particle size is at a minimum in any given system. One can discontinue adding additional cluster compound when the desired particle size has been achieved. If the aforementioned maximum amount of cluster compound is exceeded, undesirable results such as a wider particle size range and precipitation of the colloidal dispersion ensue.

Turning now to a consideration of solvents which are suitable for preparing the colloidal dispersions of the instant invention, suitable solvents must be inert in the sense that they react neither with the transition metal cluster compound, the polymer, nor the resulting transition metal dispersion. The solvent must be capable of dissolving the polymer, preferably at about ambient temperature or slightly above for convenience, and necessarily at the reaction temperature. It should likewise be a good solvent for the transition metal cluster compound preferably at about ambient temperature, and necessarily at the reaction temperature. Thus, practically speaking, the choice of a suitable solvent depends upon the transition metal cluster compound employed and the polymer employed, with due regard to the solubility and reactivity of these materials. A wide variety of inert solvents may be employed. Some solvents which have been found to be particularly useful include the following: (1) benzene and alkyl derivatives thereof such as monoalkylbenzenes and dialkylbenzenes; (2) halogenated derivatives of benzene such as chlorobenzene, o-dichlorobenzene, and p-dichlorobenzene; (3) straight chain and cyclic hydrocarbons, and particularly alkanes having from about 5 to about 20 carbon atoms, either straight chain or branched, such as decane, octane, hexadecane, pentane, iso-octane and neopentane, and cyclic alkanes such as cyclohexane, decalin and tetralin; (4) ethers and alcohols such as tetrahydrofuran, dialkyl ethers, ethyleneglycolmonomethylether, ethyleneglycolmonoethylether, butanol, hexanol and cyclohexanol; (5) esters such as alkylacetates, alkylpropionates and alkylbutyrates; and (6) ketones such as cyclohexanone, mesityl oxide, etc.

There is no particular upper limit on the boiling point of the solvent selected, but there is a practical lower limit, that being the temperature at which thermal decomposition of the polymer-bound transition metal cluster compound will proceed at the pressure employed. Concerning the melting point of the solvent, it must be a liquid at the reaction temperature of the thermal decomposition of the polymer-bound transition metal cluster compound and it should preferably be liquid at ambient temperature or slightly above ambient temperature to facilitate making the reaction mixture and subsequent processing of the resulting dispersion after the reaction is complete.

The amount of solvent to be employed depends primarily upon the polymer which is selected, and more particularly, upon the molecular weight thereof, being in mind that the concentration of the polymer in the solvent solution must be below the critical entanglement concentration for the polymer molecules, so that each polymer molecule is a discrete, individual, isolated domain, not entangled with any other polymer molecules. As a practical matter, the lowest molecular weight polymer which would ordinarily be used would have a molecular weight of about 1,000, so as to be capable of forming sizable discrete domains. With such a low molecular weight polymer, it is possible to use about 10 percent or more by weight of polymer based upon the weight of the solvent, based upon the critical entanglement concentration. Of course, one may use more solvent than the required minimum, if desired. As a practical matter, the maximum molecular weight of the polymer which may ordinarily be used is about 1 million, and with such a high molecular weight polymer, a maximum polymer concentration of about 0.5 percent by weight based upon the weight of the solvent may be used; typically, with such high molecular weight polymers, the polymer concentration which is generally preferred may range from about 0.2 percent to about 0.5 percent by weight based upon the weight of the solvent, again, the limit being based upon the critical entanglement concentration. The molecular weight of the polymer which is selected is chosen primarily with regard to the size of the colloidal transition metal particles desired; the higher concentrations of lower molecular weight range polymers will produce relatively small particles, whereas lower concentrations of higher molecular weight polymers will tend to yield larger colloidal particles. Typically, the molecular weight of the polymers ranges from about 10,000 to about 100,000, in which case the typical concentration of the polymer in the solvent ranges, respectively, from about 5 percent down to about 2 percent by weight based upon the weight of the solvent.

Concerning the reaction temperature, the solution of the polymer and transition metal cluster compound is heated at a temperature at which the polymer-bound cluster compound decomposes to the transition metal at a much more rapid rate than any unbound free cluster compound which may be in the solution decomposes to the transition metal. In practice, a suitable temperature range is from about 100° C. to about 170° C. for most systems, and the preferred temperature range for most systems is from about 140° C. to about 160° C. The optimal temperature for any given system may readily be determined simply by monitoring the rate of carbon monoxide evolution from the system. Excessive temperatures may result in an uncontrolled reaction and undesirable precipitation of transition metal particles of a micron or greater. Prior to nucleation, the rate of carbon monoxide evolution in the presence of the functional polymer is comparable to that in the absence of polymer. However, after nucleation, the rate of decomposition at the surface of the particles is much faster than that in solution. It is generally preferable to use the minimum temperature that will give a significant rate of decomposition of the polymer-bound transition metal cluster compound to the transition metal, since this also tends to minimize solution phase decomposition. The optimum temperature varies with the system and, as mentioned, is best simply determined experimentally. It is generally preferred to conduct the reaction at atmospheric pressure for convenience, although the reaction will proceed at a pressure above or below atmospheric pressure, which would, in turn, influence the boiling point of the selected solvent. The solvent, of course, must have a boiling point which is at least as high as the desired reaction temperature at the pressure employed. It is useful to select a solvent having a boiling point, at the pressure employed, such that the reaction may be carried out at reflux temperature, this being useful in that it assists the evolution of carbon monoxide. However, it is possible to operate at temperatures below reflux temperature.

As mentioned, the reaction should be carried out in an inert atmosphere, that is, inert in the sense that the atmosphere does not cause any adverse reactions in the system, either with respect to the solvent, the polymer, the transition metal cluster compound or the product. While argon is conveniently used in the examples which follow, other inert atmospheres may be employed such as nitrogen, neon and helium, or the reaction may be carried out in a vacuum with sufficiently high boiling solvents and cluster compounds.

It is to be particularly noted that the polymer is both a reactant and a catalyst for the decomposition of the transition metal cluster compound; it is not an inactive component which merely serves to stabilize independently nucleated particles.

The following examples are intended to illustrate, and not to limit, the scope of the instant invention.

EXAMPLE I

The example illustrates the preparation of a colloidal dispersion of rhodium particles prepared with a hydroxyl-terminated copoly(styrene/butadiene) (0.25/0.75) molar as the functional polymer.

40.0 g. of the aforementioned functional polymer is dissolved in 100 g. of diethyleneglycoldimethylether at ambient temperature (about 25° C.) in a 250 ml. 4-neck round bottom flask. This represents a 3.85 weight percent polymer solution. The flask is equipped with a paddle stirrer, a thermometer long enough to have its bulb immersed in the liquid, a reflux condenser, and a combined gas inlet and rubber serum cap for introducing an inert atmosphere and reactants and to permit sampling the reaction mixture with a hypodermic syringe and needle. The reflux condenser is vented to the atmosphere through a drying tube containing a dessicant. The lower portion of the flask is immersed in a mineral oil bath as a heat source.

In preparation for the introduction of the precursor hexarhodiumhexadecylcarbonyl, the solution in the flask is heated to 150° C. and the system is thoroughly purged with argon overnight for about 16 hours with the temperature being maintained at 150° C. 25.0 g. of precursor dissolved in 50 g. of diethyleneglycoldimethylether is added in twenty equal increments, generally maintaining a continuing argon flow and constant stirring. The increments are added every 2.5 hours. The progress of the reaction and the formation of polymer liganded metal carbonyl intermediates is followed by taking periodic infrared spectra of samples removed from the reaction mixture. After adding the last increment, heating is continued for about 24 hours until the precursor has been completely decomposed, as conveniently determined by the absence of the carbonylbands near 2,000 cm$^{-1}$ in the infrared spectrum of the dispersion. The dispersion is cooled to room temperature, and, under an inert atmosphere of argon, the dispersion is filtered to remove any large particles of rhodium or precipitated polymer, that is, anything flocculent. The filtration is carried out under pressure through a pad filter having pores of 2–4 microns and the filtrate is then bottled under argon in serum bottles for retention and further testing. The dispersion contains 8.6% rhodium by weight and 2.4% polymer by weight, the rhodium particles being bound to the polymer molecules. The dispersion is comprised of rhodium particles ranging from about 80–120 Angstrom units in diameter.

The instant invention provides a method for the preparation of a homogeneous, physically stable colloidal elemental transition metal dispersion, suitable for use as a catalyst, comprising colloidal transition metal particles having a particle size within the range of from about 10 Angstrom units to about 200 Angstrom units dispersed in an inert liquid and stabilized by the presence of a functional polymer to the reactive sites of which the transition metal particles are bound.

EXAMPLE II

This example illustrates the preparation of a colloidal dispersion of iridium particles using a hydroxyl-terminated poly(butadiene) as the functional polymer.

Example I is repeated, the only significant differences being that 4.0 g. of a hydroxyl-terminated poly(butadiene) is substituted for the 4.0 g. of the functional polymer employed in Example I, and 20.0 g. of tetrairidiumdodecacarbonyl is substituted for the precursor of Example I.

The resultant iridium dispersion contains 8.3 percent of iridium by weight and 2.4 percent polymer by weight, the iridium particles being bound to the polymer molecules, the dispersion comprising particles ranging from about 50–100 Angstrom units in diameter.

EXAMPLE III

This example illustrates the preparation of a colloidal dispersion of ruthenium particles using copoly(styrene/para-styryldiphenylphosphine) (9.3/0.7) molar as the functional polymer.

Example I is repeated, the only significant differences being that (1) the above-mentioned functional polymer is substituted for the functional polymer employed in Example 1; (2) only 250 g. of diethyleneglycoldimethylether is used as the inert solvent; and (3) 18.85 g. of trirutheniumdodecacarbonyl as the precursor dissolved in 50 g. of dimethyleneglycoldimethylether is added in 30 equal increments. The resulting dispersion contains 2.8 percent ruthenium by weight and 1.3 percent polymer by weight, the ruthenium particles being bound to the polymer molecules. The dispersion comprises ruthenium particles ranging from about 50–120 Angstrom units.

EXAMPLE IV

This example illustrates the preparation of a colloidal dispersion of osmium particles using copoly(styrene/para-styryldiphenylphosphine)(9.3/0.7) molar as the functional polymer.

Example III is repeated, the only significant difference being that 13.5 g. of triosmiumdodecacarbonyl is substituted for the precursor of Example III.

The resultant osmium dispersion contains 2.7 percent of osmium by weight and 1.3 percent polymer by weight, the osmium particles being bound to the polymer molecules, the dispersion comprising particles ranging from about 80–120 Angstrom units in diameter.

EXAMPLE V

This example illustrates the use of a colloidal transition metal dispersion according to the invention as a catalyst.

A colloidal rhodium dispersion prepared as in Example I is used to catalyze the hydroformylation of 1-hexene as follows. While constantly maintaining an inert atmosphere of argon, 100 g. of the dispersion is diluted to 500 ml. with xylene in a one liter capacity autoclave, and 86 g. of 1-hexene is added. The autoclave is closed and the argon is removed and replaced with a mixture of equal parts by volume of carbon monoxide and hydrogen. The temperature of the mixture is raised to 100° C., then the pressure in the autoclave is increased to 42 atmospheres with a 1:1 volume mixture of carbon monoxide and hydrogen, and the temperature and pressure are maintained for 4 hours. The pressure is then released and the reaction mixture is blanketed with an atmosphere of argon, then cooled to ambient temperature. A sample of the product of the reaction is removed and subjected to gas chromatographic analysis, which shows that 95 percent of the 1-hexene is converted to normal and iso heptaldehydes. The ratio of normal heptaldehyde to iso heptaldehyde is about 2:1 by weight.

EXAMPLE VI

This example illustrates the preparation and use of a supported colloidal transition metal particle catalyst according to the invention by means of suspension polymerization.

100 g. of colloidal rhodium dispersion prepared substantially as in Example I is vacuum concentrated to 50 percent by weight of nonvolatile material. To the concentrate is added 150 g. of styrene monomer and 2 g. of divinylbenzene monomer, resulting in a dispersion of the colloidal rhodium particles in the solution of the two monomers. 1.5 g. of stearic acid as a lubricant and 1.5 g. of azobisisobutyronitrile as a polymerization initiator in solution are dissolved in the dispersion.

A 2-liter round bottom flask equipped with a stirrer, reflux condenser and argon inlet is provided, with an oil bath as a heat source. Into the flask is introduced 500 ml. of deionized water, 0.1 g. of sodium lauryl sulfate as a surfactant, 1.5 g. of sodium polyacrylate as a dispersant and protective colloid, and 5 g. of sodium sulfate. After heating the contents of the flask to 80° C., the colloidal rhodium dispersion containing the monomers is added and the mixture is stirred vigorously at 80° C. for 4 hours under a constant argon atmosphere. During the 4 hour period, the styrene and divinylbenzene are polymerized to yield beads of cross-linked polystyrene of the order of 1 mm. in diameter containing 5.4 weight percent rhodium particles having a diameter of about 80–120 Angstrom units. The reaction mixture is cooled to room temperature, filtered, and the product catalyst beads are vacuum dried at 60° C. to yield about 150 g. of the supported catalyst.

The catalyst prepared as above is used to catalyze the hydroformylation of 1-hexene as follows. While constantly maintaining an inert atmosphere of argon, 150 g. of catalytic beads is slurried in 500 ml. of cyclohexane in a one liter capacity autoclave, and 86 g. of 1-hexene is added. The autoclave is closed and the argon is removed and replaced with a mixture of equal parts by volume of carbon monoxide and hydrogen. The temperature of the mixture is raised to 100° C., then the pressure in the autoclave is increased to 42 atmospheres with a 1:1 volume mixture of carbon monoxide and hydrogen, and the temperature and pressure are maintained for 4 hours. The pressure is then released and reaction mixture is blanketed with an atmosphere of argon, then cooled to ambient temperature. A sample of the product of the reaction is removed and subjected to gas chromatographic analysis, which shows that 90 percent of the 1-hexene is converted to normal and iso heptaldehydes. The ratio of normal heptaldehyde to iso heptaldehyde is about 2.0:1.0 by weight.

As illustrated by Example VI, the invention provides a method for the preparation of a bead-supported catalyst comprising colloidal transition metal particles having a particle size within the range of from about 10 Angstrom units to about 200 Angstrom units, said particles being bound to the reactive sites of a functional polymer, and said particles and functional polymer being supported in the beads, said method comprising supporting a liquid-dispersed colloidal elemental transition metal catalyst in beads, said beads being produced by suspension polymerization of at least one polymerizable monomer.

Depending upon the amounts of polymer and transition metal cluster compound employed, colloidal transition metal dispersions according to the invention, with the transition metal particles bound to the polymer molecules may be prepared having a weight ratio of transition metal to polymer within the range of from about 10:100 to about 90:10.

Although the invention has been described herein with reference to various preferred embodiments, it is to be understood that variations and modifications may be resorted to as will be apparent to those skilled in the art. Such variations and modifications are to be considered within the purview and the scope of the claims appended hereto.

For example, it is usual to add the polymer to the solvent and dissolve it as the first step, at room temperature, or at some higher temperature which may be as high as the temperature at which the reaction is to occur. However, this procedure could be varied, for example, by adding the first increment of the transition metal cluster compound to the solvent first, and then dissolving the polymer in the solvent, subsequently heating to the reaction temperature. It is also possible, during the reaction, to add more polymer to provide additional reactive sites to increase the number of metal particles in the system. Also, additional polymer, over and above the earliermentioned approximately 10 percent or more maximum, may be added at the end of the reaction to enhance the stability of the dispersion, depending upon the intended purpose for the dispersion. It may be preferred to use two different polymers, one being inert and the other being reactive; the inert polymer would typically, but not necessarily, be added after nucleation, and serves to enhance the stability of the resulting dispersion. One may, of course, use a plurality of transition metal cluster compounds, suitably adjusting the conditions. If it is planned to conduct a continued series of reactions using the same materials, it is possible to make a master nucleated batch of polymer-bound transition metal cluster compound for subsequent use as desired.

As another possible variation, the decomposition of the polymerbound transition metal cluster compound, while preferably and most conveniently effected by heat, may also be effected by other stimuli such as actinic radiation. Also, actinic radiation may be used to effect loss of one or more ligands from the transition metal cluster compound at ambient temperature or below, thus enabling the binding of the cluster compound to the reaction sites, of a passive polymer.

Referring to the examples, most of the functional polymers used are copolymers, but while this is preferable, it is not essential. Any suitable homopolymer containing reactive sites may be used. Preferably, however, it is desirable to copolymerize the monomer containing the binding moiety with an inert monomer, so that the inert moieties in the polymer chain reduce the number of binding sites in the entire chain, the polymer thus containing moieties having some reactive sites and also moieties not containing reactive sites. Desirably, the inert monomer is selected from the group consisting of styrene, ethylene, methylmethacrylate and vinylacetate and the comonomer containing the binding moiety is selected from the group consisting of butadiene, isoprene, cyclopentadiene, para-styryldiphenylphosphine, and parastyryldiphenylphosphine oxide.

The colloidal transition metal dispersions, if stored, should be stored under an inert atmosphere to prevent oxidation of the transition metal particles and/or other undesirable reactions.

What is claimed is:

1. A method for the preparation of a homogeneous, physically stable colloidal elemental dispersion of a transition metal selected from the group consisting of ruthenium, rhodium, osmium and iridium comprising:
    (a) preparing a solution in an inert solvent of a functional polymer, the concentration of the polymer being below its critical entanglement concentration, to provide discrete reactive binding sites to which transition metal cluster compound molecules can become bound;
    (b) incrementally adding, at suitable time intervals, a labile transition metal cluster compound, the molecules of which rapidly become bound to the reactive sites of the polymer;
    (c) maintaining a temperature which is sufficiently high to decompose the polymer-bound transition metal cluster compound much more rapidly than any transition metal cluster compound which may remain unbound in the solution decomposes to metal;
    (d) continuing the addition of increments of transition metal cluster compound to yield colloidal transition metal particles of the desired size within the range of from about 10 Angstrom units to about 200 Angstrom units, the transition metal particles being bound to the polymer molecules; and
    (e) steps (b), (c) and (d) being carried out in an inert atmosphere.

2. A method as set forth in claim 1 wherein the transition metal is ruthenium.

3. A method as set forth in claim 1 wherein the transition metal is rhodium.

4. A method as set forth in claim 1 wherein the transition metal is osmium.

5. A method as set forth in claim 1 wherein the transition metal is iridium.

6. A method as set forth in claim 1 wherein the final increment, after decomposition, yields colloidal transition metal particles having a maximum size of about 150 Angstrom units.

7. A method as set forth in claim 1 wherein the transition metal cluster compound increments are added when only a little or no carbon monoxide is being generated.

8. A method as set forth in claim 1 wherein the transition metal cluster compound increments are added from about 2 to about 4 hours apart.

9. A method as set forth in claim 1 which is carried out at about atmospheric pressure.

10. A method as set forth in claim 1 wherein the addition of the transition metal cluster compound is continuous, at a rate sufficient to compensate for the consumption of the transition metal cluster compound already added.

11. A method as set forth in claim 1 wherein the sufficiently high temperature is reflux temperature.

12. A method as set forth in claim 1 wherein the sufficiently high temperature is within the range of from about 100° C. to about 170° C.

13. A method as set forth in claim 12 wherein the temperature is within the range of from about 140° C. to about 160° C.

14. A method as set forth in claim 1 wherein the sufficiently high temperature is the minimum temperature that will cause a significant rate of decomposition of the polymer-bound transition metal cluster compound.

15. A method as set forth in claim 1 wherein decomposition of the polymer-bound transition metal cluster compound to the transition metal is effected by actinic radiation instead of heat.

16. A method as set forth in claim 1 wherein the binding of the transition metal cluster compound to the functional polymer is effected by actinic radiation.

17. A method as set forth in claim 1 wherein additional polymer is added during the reaction.

18. A method as set forth in claim 1 wherein additional polymer is added after the reaction is complete.

19. A method as set forth in claim 1 wherein the polymer is soluble in the inert solvent at about ambient temperature.

20. A method as set forth in claim 1 wherein the polymer is a homopolymer.

21. A method as set forth in claim 1 wherein the polymer is a copolymer of a reactive monomer and an inert monomer.

22. A method as set forth in claim 21 wherein said copolymer is prepared by polymerization of vinyl type monomers.

23. A method as set forth in claim 21 wherein the inert monomer is selected from the group consisting of styrene, ethylene, methylmethacrylate and vinylacetate and the reactive monomer is selected from the group consisting of butadiene, isoprene, cyclopentadiene, para-styryldiphenylphosphine, and para-distyrylphosphine oxide.

24. A method as set forth in claim 1 wherein said polymer has a molecular weight of from about 1000 to about 1 million.

25. A method as set forth in claim 24 wherein the polymer concentration in the solution is, respectively, from about 10 percent or more to about 0.2–0.5 percent by weight based upon the weight of the solvent.

26. A method as set forth in claim 1 wherein said polymer has a molecular weight of from about 10,000 to about 100,000.

27. A method as set forth in claim 26 wherein the polymer concentration in the solution is, respectively, from about 5 percent to about 2 percent by weight based upon the weight of the solvent.

28. A method as set forth in claim 1 wherein said inert solvent is a liquid at about ambient temperature.

29. A method as set forth in claim 1 wherein said transition metal cluster compound is a carbonyl cluster compound.

30. A method as set forth in claim 29 wherein said transition metal carbonyl cluster compound is hexarhodiumhexadecacarbonyl.

31. A method as set forth in claim 29 wherein said transition metal carbonyl cluster compound is tetrarhodiumdodecacarbonyl.

32. A method as set forth in claim 29 wherein said transition metal carbonyl cluster compound is tetrairidiumdodecacarbonyl.

33. A method as set forth in claim 29 wherein said transition metal carbonyl cluster compound is triosmiumdodecacarbonyl.

34. A method as set forth in claim 29 wherein transition metal cluster compound is trirutheniumdodecacarbonyl.

35. A homogeneous, physically stable colloidal elemental dispersion of a transition metal selected from the group consisting of ruthenium, rhodium, osmium and iridium, suitable for use as a catalyst, comprising colloidal transition metal particles having a particle size within the range of from about 10 Angstrom units to about 200 Angstrom units dispersed in an inert liquid and stabilized by the presence of a functional polymer to the reactive sites of which the transition metal particles are bound, said dispersion being prepared by the method of claim 1.

36. A dispersion as set forth in claim 35 wherein the transition metal is ruthenium.

37. A dispersion as set forth in claim 35 wherein the transition metal is rhodium.

38. A dispersion as set forth in claim 35 wherein the transition metal is osmium.

39. A dispersion as set forth in claim 35 wherein the transition metal is iridium.

40. A dispersion as set forth in claim 35 having a maximum colloidal transition metal particle size of about 150 Angstrom units.

41. A dispersion as set forth in claim 35 wherein the weight ratio of transition metal to polymer is within the range of from about 90:100 to about 90:10.

42. A method for the preparation of a bead-supported catalyst comprising colloidal particles of a transition metal selected from the group consisting of ruthenium, rhodium, osmium and iridium having a particle size within the range of from about 10 Angstrom units to about 200 Angstrom units, said particles being bound to the reactive sites of a functional polymer, and said particles and polymer being supported in the beads, said method comprising supporting a liquid-dispersed colloidal elemental transition metal catalyst as set forth in claim 35 in beads, said beads being produced by suspension polymerization of at least one polymerizable monomer.

43. A method as set forth in claim 42 wherein the transition metal is ruthenium.

44. A method as set forth in claim 42 wherein the transition metal is rhodium.

45. A method as set forth in claim 42 wherein the transition metal is osmium.

46. A method as set forth in claim 42 wherein the transition metal is iridium.

47. A bead-supported catalyst as set forth in claim 42 wherein the beads comprise cross-linked polystyrene.

* * * * *